United States Patent
Kikuchi

(10) Patent No.: US 10,367,974 B2
(45) Date of Patent: Jul. 30, 2019

(54) IMAGE PROCESSING APPARATUS, IMAGE PROCESSING METHOD, PROGRAM, AND ENDOSCOPE SYSTEM

(71) Applicant: SONY CORPORATION, Tokyo (JP)

(72) Inventor: Daisuke Kikuchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 162 days.

(21) Appl. No.: 15/321,205

(22) PCT Filed: Jun. 23, 2015

(86) PCT No.: PCT/JP2015/067944
§ 371 (c)(1),
(2) Date: Dec. 22, 2016

(87) PCT Pub. No.: WO2016/006429
PCT Pub. Date: Jan. 14, 2016

(65) Prior Publication Data
US 2017/0155804 A1    Jun. 1, 2017

(30) Foreign Application Priority Data

Jul. 7, 2014 (JP) ................................. 2014-139506

(51) Int. Cl.
*A61B 1/04* (2006.01)
*G06T 1/00* (2006.01)
(Continued)

(52) U.S. Cl.
CPC .............. *H04N 1/6016* (2013.01); *A61B 1/04* (2013.01); *G02B 23/24* (2013.01);
(Continued)

(58) Field of Classification Search
CPC ............... H04N 1/6016; H04N 5/2256; H04N 2005/2255; G02B 23/2484; A61B 1/04
See application file for complete search history.

(56) References Cited

U.S. PATENT DOCUMENTS

2005/0036668 A1* 2/2005 McLennan ........... G06K 9/4652
382/128
2007/0247475 A1* 10/2007 Pettigrew ................ G09G 5/06
345/594
(Continued)

FOREIGN PATENT DOCUMENTS

JP          6-282630 A      10/1994
JP      2005-348902 A      12/2005
(Continued)

OTHER PUBLICATIONS

Noorhayati (Fish Bone Impaction Using Adaptive Histogram Equalization (AHE), 978-0-7695-4043-6/1 2010 IEEE).*
(Continued)

*Primary Examiner* — Christopher S Kelley
*Assistant Examiner* — Nasim N Nirjhar
(74) *Attorney, Agent, or Firm* — Oblon, McClelland, Maier & Neustadt, L.L.P.

(57) ABSTRACT

The present disclosure relates to an image processing apparatus, an image processing method, a program, and an endoscope system capable of obtaining an image with high color discrimination. A histogram generation unit generates histograms of pixel values for an input image regarding luminance Y, saturation S, and hue H. A histogram correction unit subtracts components of the saturation, the luminance, and the hue of a portion determined to be a foreign object by a foreign object detection unit from the histograms regarding the saturation, the luminance, and the hue generated by the histogram generation unit and then weights by a value of a standard histogram. The present disclosure may be applied to the endoscope system which performs color conversion on an image input from a camera head through a scope, for example.

14 Claims, 8 Drawing Sheets

(51) Int. Cl.
*H04N 1/46* (2006.01)
*H04N 1/60* (2006.01)
*G02B 23/24* (2006.01)
*H04N 5/225* (2006.01)

(52) U.S. Cl.
CPC ............ *G02B 23/2484* (2013.01); *G06T 1/00* (2013.01); *H04N 1/46* (2013.01); *H04N 1/60* (2013.01); *H04N 5/2256* (2013.01); *H04N 2005/2255* (2013.01)

(56) References Cited

U.S. PATENT DOCUMENTS

| | | |
|---|---|---|
| 2013/0343646 A1 | 12/2013 | Hata et al. |
| 2017/0046836 A1* | 2/2017 | Bramwell ............... G06T 5/007 |

FOREIGN PATENT DOCUMENTS

| | | |
|---|---|---|
| JP | 2006-173823 A | 6/2006 |
| JP | 2007-257087 A | 10/2007 |
| JP | 2008-132321 A | 6/2008 |
| JP | 2011-015738 A | 1/2011 |
| JP | 2013-146937 A | 8/2013 |
| JP | 2014-007611 A | 1/2014 |

OTHER PUBLICATIONS

International Search Report and Written Opinion of PCT Application No. PCT/JP2015/067944, dated Aug. 18, 2015, 11 pages of English Translation and 22 pages of ISRWO.

International Preliminary Report on Patentability of PCT Application No. PCT/JP2015/067944, dated Jan. 19, 2017, 11 pages of English Translation and 19 pages of IPRP.

\* cited by examiner

IMAGE PROCESSING APPARATUS, IMAGE PROCESSING METHOD, PROGRAM, AND ENDOSCOPE SYSTEM

CROSS REFERENCE TO RELATED APPLICATIONS

This application is a U.S. National Phase of International Patent Application No. PCT/JP2015/067944 filed on Jun. 23, 2015, which claims priority benefit of Japanese Patent Application No. JP 2014-139506 filed in the Japan Patent Office on Jul. 7, 2014. Each of the above-referenced applications is hereby incorporated herein by reference in its entirety.

TECHNICAL FIELD

The present disclosure relates to an image processing apparatus, an image processing method, a program, and an endoscope system, and especially relates to the image processing apparatus, the image processing method, the program, and the endoscope system capable of obtaining an image with high color discrimination.

BACKGROUND ART

In an endoscope apparatus including a color conversion process such as LUT, a set value of a conversion parameter is generally determined in advance; when a type of an input image and an environment such as illumination change, a user manually switches the set value and the like. Since the set value is manually set in advance, it is difficult to set an optimal parameter according to a situation, and it is difficult to obtain an output image adjusted to have an optimal color by this, so that it is required to automatically obtain an image with high color discrimination.

In response to such a situation, there are suggestion to change color reproduction according to a light source type (refer to Patent Document 1) and suggestion to switch a system color tone for each organ being observed (refer to Patent Document 2).

CITATION LIST

Patent Document

Patent Document 1: Japanese Patent Application Laid-Open No. 2008-132321
Patent Document 2: Japanese Patent Application Laid-Open No. 2005-348902

SUMMARY OF THE INVENTION

Problems to be Solved by the Invention

Herein, a living body image has biased color distribution and almost similar colors often occupy a screen. For example, reddish colors and whitish colors occupy a large part of an image in the abdominal cavity and an image regarding a field of orthopedics, respectively. Therefore, it is required to discriminate tissue among similar colors, so that color discrimination is often deteriorated. Therefore, in addition to the above-described suggestion, it is further required to improve the color discrimination in the endoscope apparatus.

The present disclosure is achieved in view of such a situation and it is possible to obtain the image with high color discrimination.

Solutions to Problems

An image processing apparatus according to an aspect of the present disclosure is provided with a histogram generation unit which generates a histogram of pixel values for an input image biased to a specific color system, and a parameter generation unit which generates a color conversion parameter for a color conversion process on the input image by arranging a point of a grid in a space of 3D-LUT on the basis of the histogram generated by the histogram generation unit.

A histogram correction unit which corrects the histogram generated by the histogram generation unit by using a standard histogram of pixel values obtained according to statistics of an image biased to the specific color system may be further provided.

A foreign object detection unit which detects a foreign object from the image is further provided, and the histogram correction unit may correct the histogram generated by the histogram generation unit by eliminating the foreign object detected by the foreign object detection.

A light source estimation unit which estimates a light source from the histogram generated by the histogram generation unit is further provided, and the histogram correction unit may correct the histogram generated by the histogram generation unit according to the light source estimated by the light source estimation unit.

The histogram of the pixel values is the histogram regarding at least a color.

The histogram of the pixel values is the histogram regarding hue, saturation, and luminance.

The histogram correction unit may correct the histogram generated by the histogram generation unit by obtaining a product of the histogram generated by the histogram generation unit and the standard histogram to weight.

The parameter generation unit may densely arrange points of the grid in the space of the LUT for a portion with high frequency.

The input image is the image biased to reddish colors, and the parameter generation unit may densely arrange the points of the grid in the space of the LUT for the reddish colors.

The input image is the image biased to whitish colors, and the parameter generation unit may densely arrange the points of the grid in the space of the LUT for the whitish colors.

The input image is the image biased to yellowish colors, and the parameter generation unit may densely arrange the points of the grid in the space of the LUT for the yellowish colors.

The parameter generation unit may generate the color conversion parameter by displacing distribution of points of the grid arranged in the space of the LUT.

A foreign object detection unit which detects a foreign object from the image is further provided, and the histogram correction unit may correct the histogram generated by the histogram generation unit after eliminating the foreign object detected by the foreign object detection.

The foreign object detection unit may detect the foreign object from the image by using the histogram generated by the histogram generation unit and the standard histogram.

A standard histogram selection unit which selects the standard histogram according to a light source is further provided, and the histogram correction unit may correct the histogram generated by the histogram generation unit by using the standard histogram selected by the standard histogram selection unit.

A light source estimation unit which estimates the light source from the histogram generated by the histogram generation unit is further provided, and the standard histogram selection unit may select the standard histogram according to the light source estimated by the light source estimation unit.

A color conversion processor which performs a color conversion process on the input image according to the parameter generated by the parameter generation unit may be further provided.

In an image processing method according to an aspect of the present disclosure, an image processing apparatus generates a histogram of pixel values for an input image biased to a specific color system, and generates a color conversion parameter for a color conversion process on the input image by arranging a point of a grid in a space of 3D-LUT on the basis of the generated histogram.

A program according to an aspect of the present disclosure allows a computer to serve as a histogram generation unit which generates a histogram of pixel values for an input image biased to a specific color system, and a parameter generation unit which generates a color conversion parameter for a color conversion process on the input image by arranging a point of a grid in a space of 3D-LUT on the basis of the histogram generated by the histogram generation unit.

An endoscope system according to an aspect of the present disclosure is provided with a scope, a camera head, a histogram generation unit which generates a histogram of pixel values for an input image biased to a specific color system input from the camera head through the scope, and a parameter generation unit which generates a color conversion parameter for a color conversion process on the input image by arranging a point of a grid in a space of 3D-LUT on the basis of the histogram generated by the histogram generation unit.

According to an aspect of the present disclosure, a histogram of pixel values is generated for an input image biased to a specific color system. Then, by arranging a point of a grid in a space of 3D-LUT on the basis of a standard histogram of pixel values obtained according to statistics of an image biased to the specific color system, the generated histogram is corrected, and a color conversion parameter for a color conversion process on the input image is generated by using the corrected histogram.

Effects of the Invention

According to the present disclosure, it is possible to perform the color conversion on the image. Especially, it is possible to obtain the image with high color discrimination.

Meanwhile, an effect disclosed in this specification is merely an example; an effect of the present technology is not limited to that disclosed in this specification and an additional effect may also be obtained.

MODE FOR CARRYING OUT THE INVENTION

Modes for carrying out the present disclosure (hereinafter, referred to as embodiments) are hereinafter described. Meanwhile, the description is given in the following order.
1. First Embodiment (Endoscope System)
2. Second Embodiment (Computer)
<First Embodiment>
<Configuration Example of System>

Figure 1:
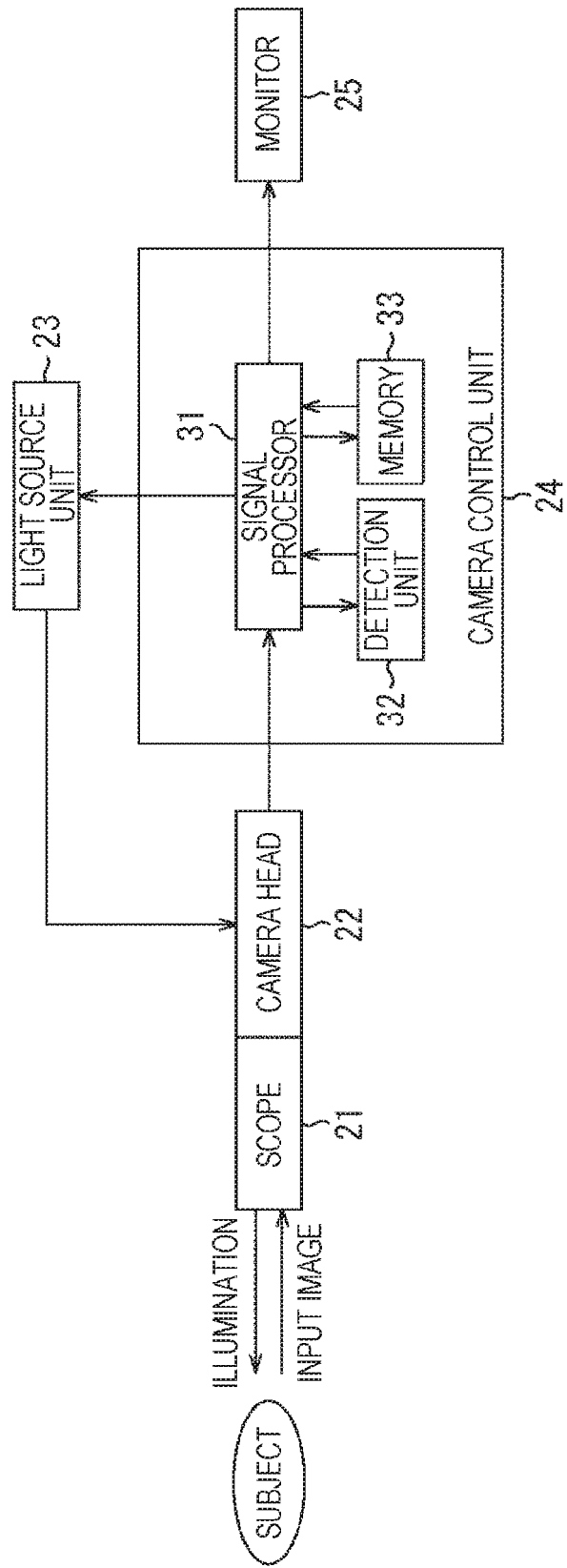
FIG. 1 is a block diagram illustrating a configuration example of an endoscope system to which the present technology is applied.

FIG. 1 is a block diagram illustrating a configuration example of an endoscope system to which the present technology is applied.

In the example in FIG. 1, an endoscope system 11 is formed of an integrated scope (endoscope) 21, a camera head 22, a light source unit 23, a camera control unit (CCU) 24, and a monitor 25.

The CCU 24 includes a signal processor 31 which controls the light source unit 23 and performs signal processing, a detection unit 32 which detects a feature of an image from an input image, and a memory 33 which stores a conversion parameter and a signal processing result.

The light source unit 23 outputs illumination of certain specific light (for example, white light) under the control of the signal processor 31. The illumination output from the light source unit 23 is input to the camera head 22 to be emitted to a subject through the scope 21. The camera head 22 takes an image of the subject. That is to say, the camera head 22 inputs the light emitted to the subject through the scope 21 and supplies the same to the signal processor 31 of the CCU 24 as the image.

The signal processor 31 performs image processing on the image from the camera head 22 on the basis of data of the image feature detected by the detection unit 32 and data read from the memory 33.

The image input from the camera head 22 being a living body image has biased color distribution and substantially similar colors often occupy a screen. That is to say, the image is the image biased to a certain specific color system. For example, reddish colors, whitish colors, and yellowish colors occupy a large part of an image in the abdominal cavity, an image regarding a field of orthopedics, and an image of the gallbladder and fat, respectively. Therefore, tissue is discriminated among similar colors, so that color discrimination is deteriorated.

In response to this, the signal processor 31 performs the image processing for improving the color discrimination on the image biased to the specific color system as described above. The image processing is sequentially described later in detail. The signal processor 31 outputs the image after the image processing to the monitor 25. The monitor 25 formed of an LCD and the like outputs the image from the signal processor 31.

Figure 2:
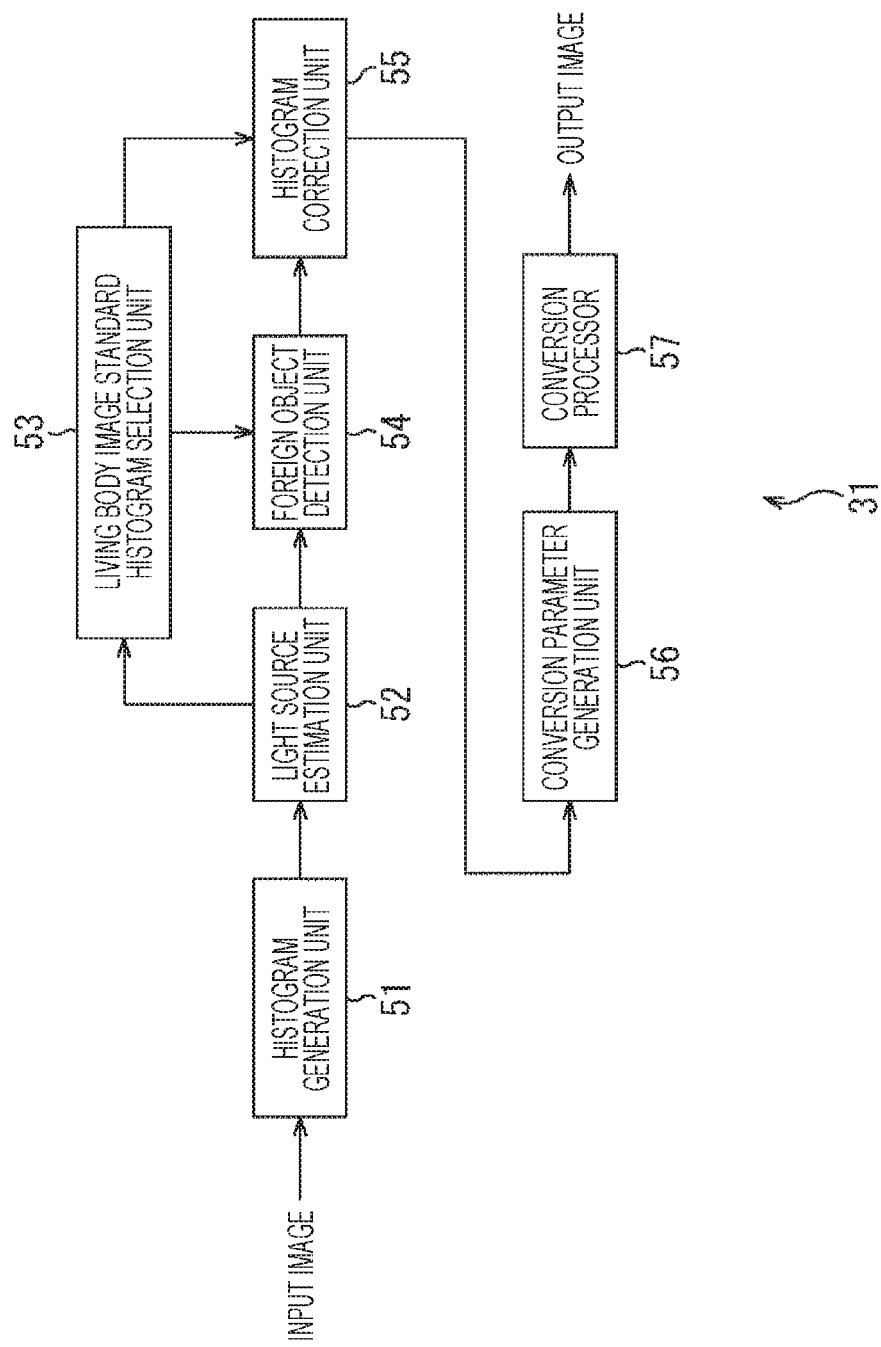
FIG. 2 is a block diagram illustrating a configuration example of a signal processor.

FIG. 2 is a block diagram illustrating a configuration example of the signal processor.

In the example in FIG. 2, the signal processor 31 includes a histogram generation unit 51, a light source estimation unit 52, a living body image standard histogram selection unit 53, a foreign object detection unit 54, a histogram correction unit 55, a conversion parameter generation unit 56, and a conversion processor 57.

The histogram generation unit 51 generates histograms of pixel values for the input image regarding luminance Y, saturation S, and hue H. An input RGB image is converted to a YCbCr image. Then, the saturation S and the hue H are obtained from Cb and Cr of an input pixel value (Y, Cb, Cr) by using following equation (1).

[Mathematical Formula 1]

$$h = \mathrm{atan}\left(\frac{Cr}{Cb}\right) \quad s = \sqrt{Cr^2 + Cb^2} \qquad (1)$$

Figure 3:
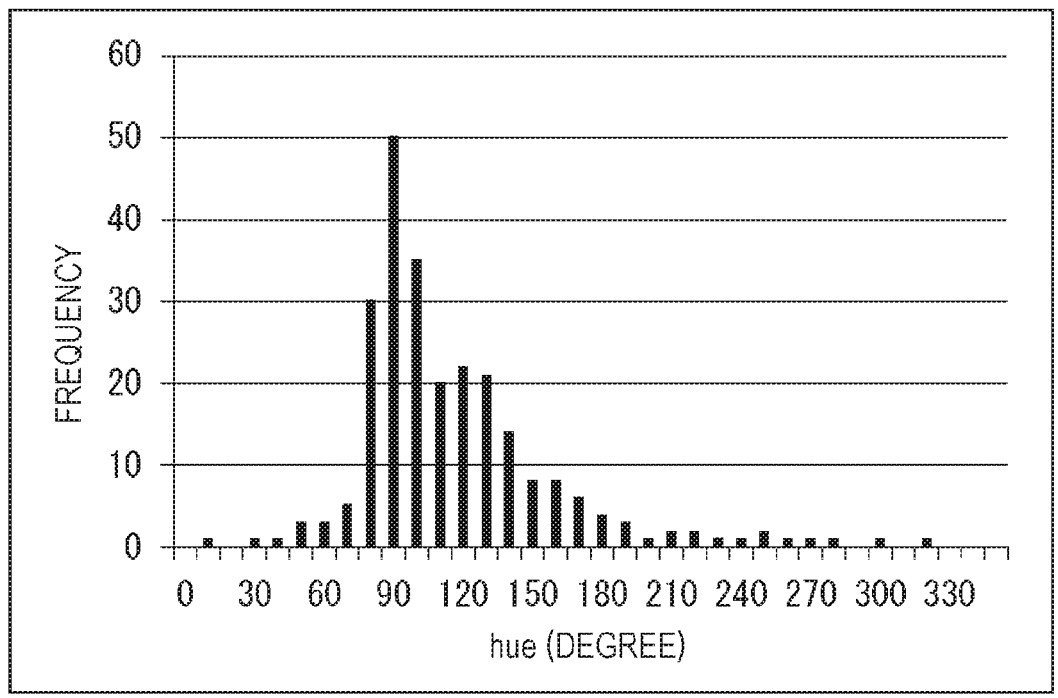
FIG. 3 is a view illustrating an example of a histogram representing frequency of hue.
Figure 4:
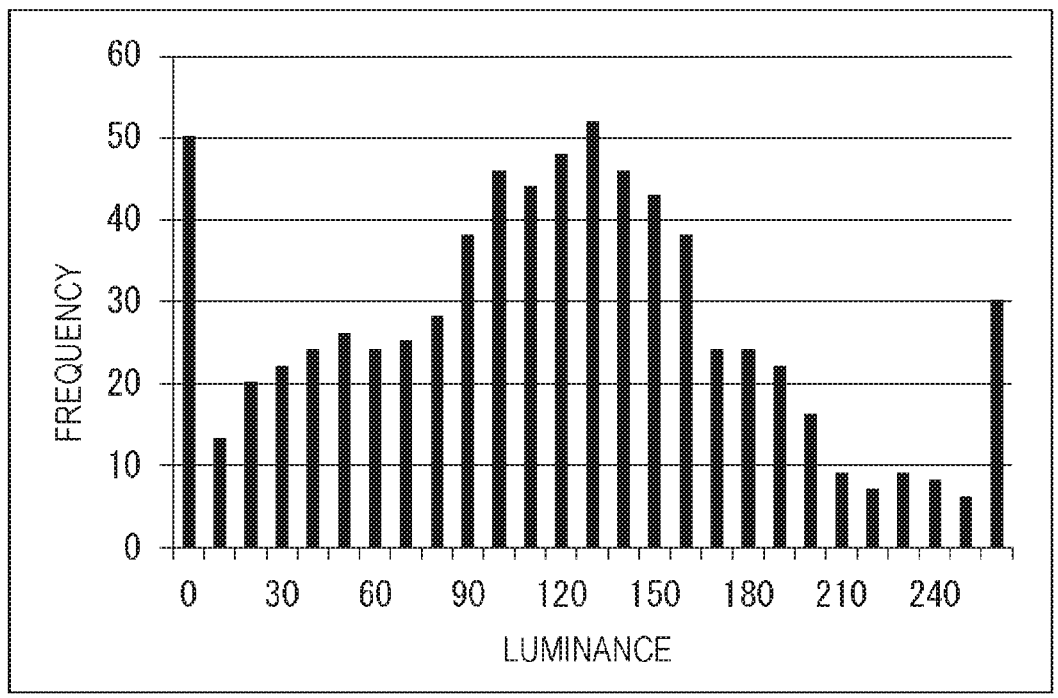
FIG. 4 is a view illustrating an example of a histogram representing frequency of luminance.
Figure 5:
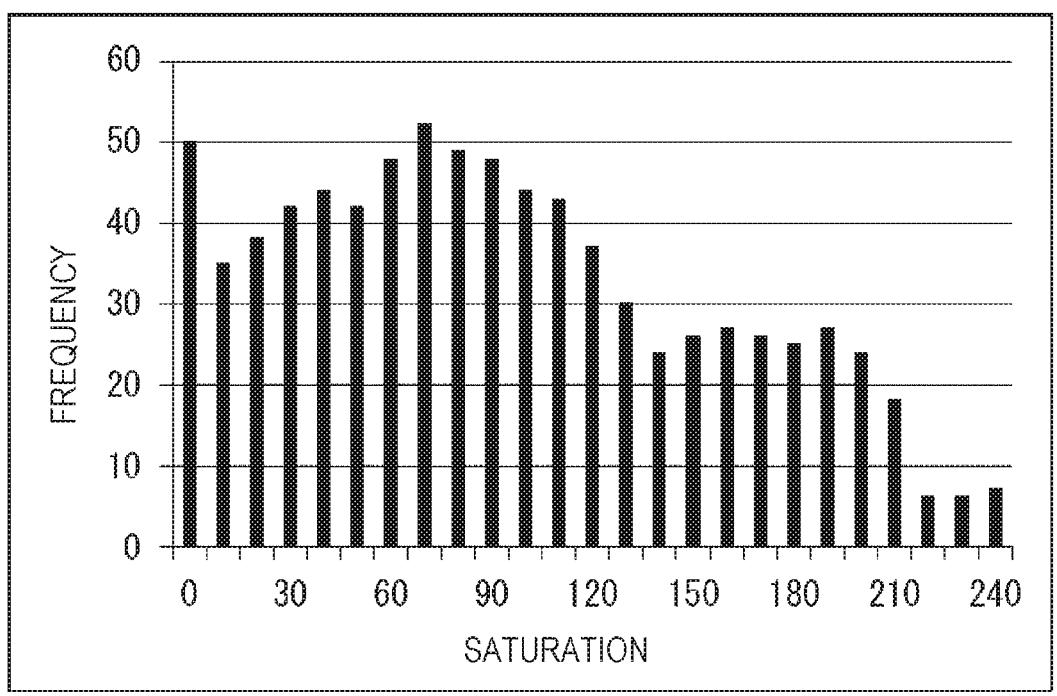
FIG. 5 is a view illustrating an example of a histogram representing frequency of saturation.

Herein, FIGS. 3 to 5 illustrate examples of the histograms. The histogram in FIG. 3 is the histogram representing frequency regarding the hue. The histogram in FIG. 4 is the histogram representing frequency regarding the luminance. The histogram in FIG. 5 is the histogram representing frequency regarding the saturation.

The histogram generation unit 51 supplies the input image and each generated histogram to the light source estimation unit 52. The light source estimation unit 52 estimates a type of a light source on the basis of the generated histogram. The light source includes a normal white light source and special light. The special light emits only light of a specific wavelength, so that this may be determined by the histogram of the hue. The light source estimation unit 52 supplies information of the estimated type of the light source to the living body image standard histogram selection unit 53. Also, the light source estimation unit 52 supplies the input image and the histogram generated by the histogram generation unit 51 to the foreign object detection unit 54 after estimating the light source.

The living body image standard histogram selection unit 53 includes a standard histogram of the living body image different for each light source obtained as a statistical value of the living body image. The standard histogram is determined depending on the type of the light source. The living body image standard histogram selection unit 53 selects the standard histogram by the light source estimated by the light source estimation unit 52 and supplies the selected standard histogram to the foreign object detection unit 54 and the histogram correction unit 55.

Since the image regarding surgery is biased to reddish colors and the image regarding cerebral surgery is biased to whitish colors, for example, each department (that is to say, each biased color system) may have its own standard histogram.

The foreign object detection unit 54 detects a foreign object from the generated histogram by using the histogram generated by the histogram generation unit 51 and the standard histogram from the living body image standard histogram selection unit 53. Herein, the foreign object is intended to mean an object other than living body tissue such as gauze, forceps, and a mask portion of a hard mirror. It is often not required that color reproducibility and color discrimination of them are especially improved, and they may be estimated from difference between the standard histogram and the generated histogram. This is because, if distribution clearly different from that of the standard histogram is included in the generated histogram, the distribution is extremely unlikely to be that of the living body tissue.

For the above-described reason, a portion which is clearly not the living body tissue is eliminated from the generated histograms of the saturation, the luminance, and the hue by the following histogram correction unit 55. The foreign object detection unit 54 supplies the input image, the generated histogram, and information of the detected foreign object to the histogram correction unit 55.

The histogram correction unit 55 corrects the histogram by combining the standard histogram selected by the living body image standard histogram selection unit 53 and the histogram eliminated by detection of the foreign object.

That is to say, the histogram correction unit 55 subtracts components of the saturation, the luminance, and the hue of the portion determined to be the foreign object from the generated histograms regarding the saturation, the luminance, and the hue, and then weights by a value of the standard histogram. This is because a portion with a larger value in the standard histogram is more likely to be the living body image and a process of placing emphasis on this to improve visibility is desired.

Specifically, the histogram correction unit 55 obtains a product of the generated histogram and the standard histogram and regards the same as a weighted histogram. By this process, the histogram is corrected to the histogram with a large weight on an important portion in terms of the saturation, the luminance, and the hue. The histogram correction unit 55 supplies the input image and the corrected histogram to the conversion parameter generation unit 56.

Figure 6:
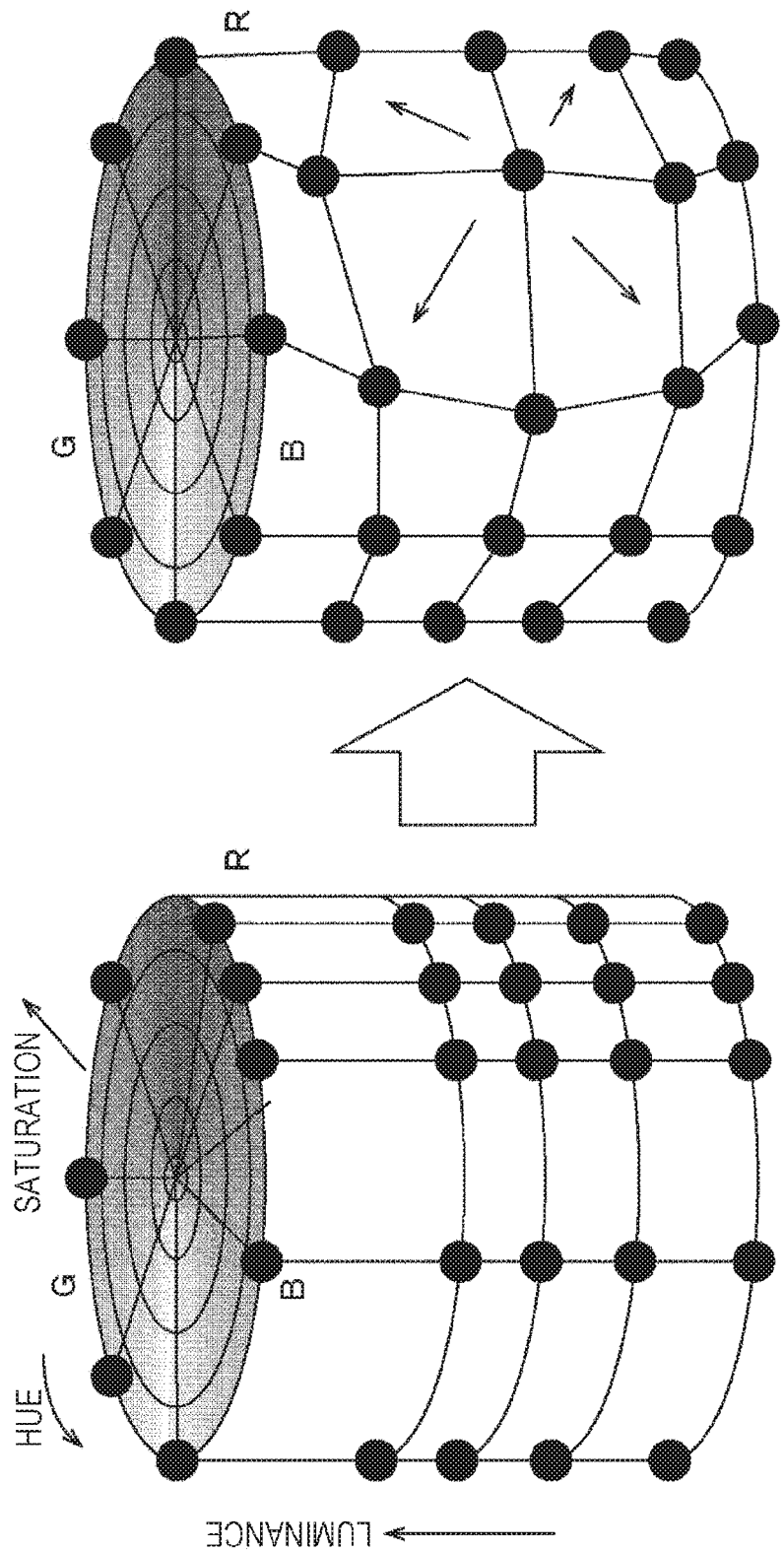
FIG. 6 is a view illustrating an example of 3D-LUT.

The conversion parameter generation unit 56 generates a color conversion parameter for a conversion process by the conversion processor 57. The conversion processor 57 performs 3D-LUT in a cylindrical HSL space as illustrated in FIG. 6. The conversion parameter generation unit 56 determines an arrangement position of a grid and a displacement parameter at each lattice point in the 3D-LUT. Those determined by the conversion parameter generation unit 56 are collectively referred to as color conversion parameters.

As for the arrangement position of the grid, the conversion parameter generation unit 56 densely arranges the grid in a portion with high frequency in the histogram corrected by the histogram correction unit 55. Specifically, the conversion parameter generation unit 56 arranges the grid such that a grid interval corresponds to an inverse number of the frequency of the histogram regarding the hue, the saturation, and the luminance and normalizes an entire length.

When the frequency of the histogram, an n-th grid arrangement coordinate, and a reference grid interval are represented by f(x), P(n), and d, respectively, following equation (2) is satisfied.

[Mathematical Formula 2]

$$P(n+1) = P(n) + \alpha * d/f(x) \qquad (2)$$

Herein, α represents a coefficient which adjusts an effectiveness level.

The conversion parameter generation unit 56 obtains the position of the grid for each axis from the above-described equation and normalizes by an entire distance for the luminance, the saturation, and the hue. According to this, as illustrated on a left side in FIG. 6, the grid is densely arranged in an important portion (portion with high frequency) in the space.

Next, the conversion parameter generation unit 56 generates the displacement parameter at each lattice point.

Regarding this, when emphasis is placed on the color reproduction, the displacement parameter to approach a target color space may be provided to each lattice point obtained above.

For example, the grid is densely arranged in the portion with high frequency as illustrated on the left side in FIG. 6, and the displacement parameter may be such that the lattice point is displaced to spread the dense portion more for the lattice point of the denser grid as illustrated on a right side in FIG. 6.

In this manner, it is possible to spread the distribution in the color space for the discrimination of which is deteriorated because this occupies a large part in the image, so that difference between portions with subtly different colors increases and the discrimination may be improved.

Specifically, a process opposite to the previous process may be performed, so that when a position after the displacement of an n-th lattice point, the position before the displacement of the n-th lattice point, and a coefficient which adjusts the level are represented by Q(n), P(n), and β respectively, an equation such as following equation (3) is satisfied.

[Mathematical Formula 3]

$$Q(n+1)=Q(n)+\beta(P(n+1)-P(n))*f(x) \quad (3)$$

By obtaining the position of each lattice point after the displacement to obtain difference between the same and the position before the displacement by equation (3) described above, the displacement parameter at each lattice point may be obtained.

The conversion parameter generation unit 56 supplies the input image and the color conversion parameter obtained in the above-described manner to the conversion processor 57.

When the conversion processor 57 performs the cylinder-side 3D-LUT process of the HSL space on the input image according to the color conversion parameter generated by the conversion parameter generation unit 56, a color conversion process illustrated in FIG. 6 is applied. That is to say, the process of spreading the distribution in the color space is performed on the pixel of the color which more frequently appears and the color discrimination is improved. The conversion processor 57 outputs the image subjected to the color conversion process to the monitor 25.

<Example of Process>

A process of the endoscope system is next described with reference to a flowchart in FIG. 7.

At step S11, the light source unit 23 outputs the illumination of the certain specific light under the control of the signal processor 31. The illumination output from the light source unit 23 is input to the camera head 22 to be emitted to a subject through the scope 21.

At step S12, the camera head 22 takes an image of the subject. That is to say, the camera head 22 inputs the light emitted to the subject through the scope 21 and supplies the same to the signal processor 31 of the CCU 24 as the image.

The signal processor 31 performs the image processing on the image from the camera head 22 at step S13. The image processing is described later in detail with reference to FIG. 8. The image subjected to the image processing at step S13 is output to the monitor 25.

At step S14, the monitor 25 displays the image from the signal processor 31.

Figure 7:
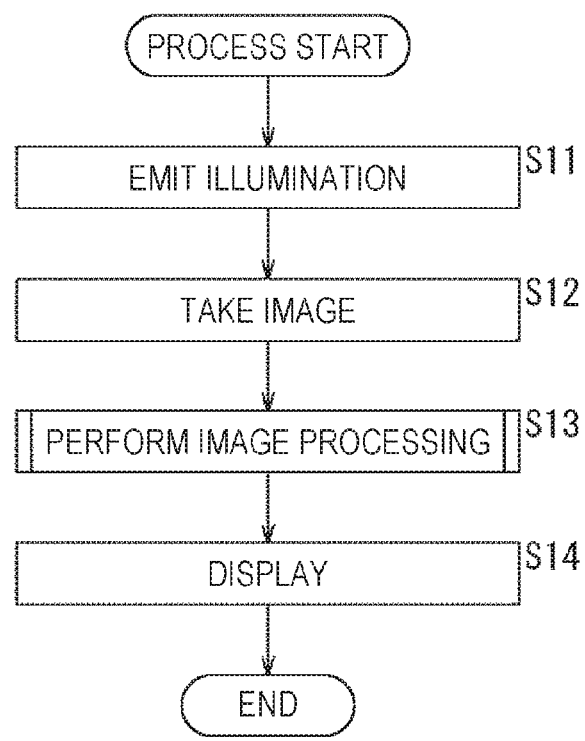
FIG. 7 is a flowchart illustrating a process of the endoscope system.
Figure 8:
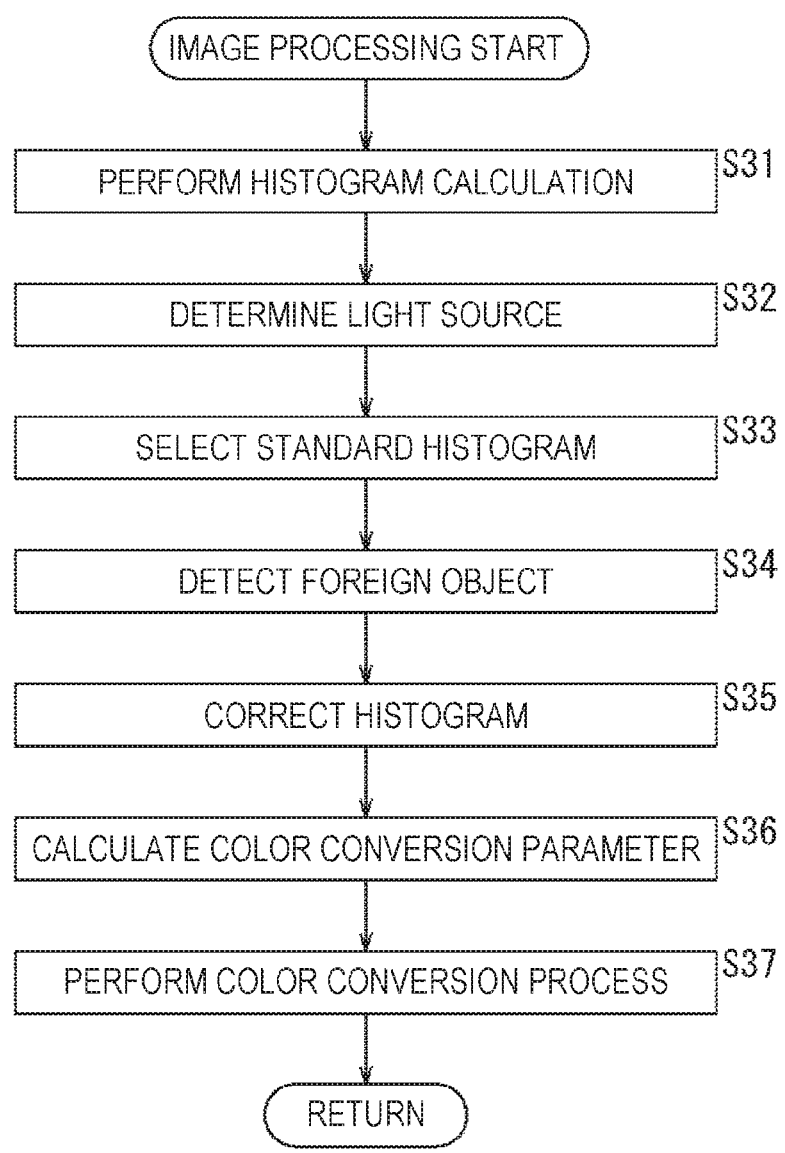
FIG. 8 is a flowchart illustrating image processing at step S13 in FIG. 7.

Next, the image processing at step S13 in FIG. 7 is described with reference to a flowchart in FIG. 8.

The image from the camera head 22 is input to the histogram generation unit 51. At step S31, the histogram generation unit 51 performs histogram calculation of the input image.

That is to say, the histogram generation unit 51 generates the histograms of the pixel values for the input image regarding the luminance Y, the saturation S, and the hue H. The histogram generation unit 51 supplies the input image and each generated histogram to the light source estimation unit 52.

At step S32, the light source estimation unit 52 determines the light source on the basis of the histogram generated at step S31 to estimate the type of the light source. The light source estimation unit 52 supplies information of the estimated type of the light source to the living body image standard histogram selection unit 53. Also, the light source estimation unit 52 supplies the input image and the histogram generated by the histogram generation unit 51 to the foreign object detection unit 54 after estimating the light source.

At step S33, the living body image standard histogram selection unit 53 selects the standard histogram by the light source estimated by the light source estimation unit 52 and supplies the selected standard histogram to the foreign object detection unit 54 and the histogram correction unit 55.

At step S34, the foreign object detection unit 54 detects the foreign object from the histogram generated at step S32. This detects the foreign object by using the histogram generated by the histogram generation unit 51 and the standard histogram from the living body image standard histogram selection unit 53. The foreign object detection unit 54 supplies the input image, the generated histogram, and information of the detected foreign object to the histogram correction unit 55.

At step S35, the histogram correction unit 55 corrects the histogram. That is to say, the histogram correction unit 55 eliminates the foreign object detected at step S34 from the histogram generated at step S32 and combines the standard histogram selected at step S34 and the histogram eliminated by the detection of the foreign object to correct the histogram.

The histogram correction unit 55 supplies the input image and the corrected histogram to the conversion parameter generation unit 56.

The conversion parameter generation unit 56 calculates to generate the color conversion parameter for the conversion process by the conversion processor 57 at step S36.

Specifically, the conversion processor 57 performs the 3D-LUT in the cylindrical HSL space as illustrated in FIG. 6. The conversion parameter generation unit 56 determines an arrangement position of a grid and a displacement parameter at each lattice point in the 3D-LUT. Those determined by the conversion parameter generation unit 56 are collectively referred to as color conversion parameters. The conversion parameter generation unit 56 supplies the input image and the color conversion parameter obtained in the above-described manner with reference to FIG. 6 to the conversion processor 57.

At step S37, the conversion processor 57 performs the cylinder-side 3D-LUT process of the HSL space on the input image according to the color conversion parameter generated at step S36, thereby performing the color conversion process.

From above, the process of spreading the distribution in the color space is performed on the pixel of the color (system) which more frequently appears and the color discrimination is improved. The conversion processor 57 outputs the image subjected to the color conversion process to the monitor 25.

Meanwhile, although the example of estimating the light source from the input image is described above, it is also possible that the signal processor 31 which controls the light source unit 23 maintains the information of the light source in advance. In this case, the light source estimation unit 52 may be removed from the signal processor 31.

Also, although the example of using three types of one-dimensional histograms by the histogram generation unit 51 and the histogram correction unit 55 is described above, it is also possible to calculate by directly using a three-dimensional histogram obtained by making them three-dimensional.

Furthermore, although the example of automatically determining the arrangement of the grid by the conversion parameter generation unit 56 and the conversion processor 57 is described above, it is also possible to set to manually determine a point on the process at which emphasis is especially wanted to be put.

Also, although the example of estimating from the histogram by the foreign object detection unit 54 is described above, it is also possible to detect by a general image detecting method.

Furthermore, although the example of the process for improving the color discrimination by the conversion parameter generation unit 56 is described above, it is also possible to perform the color conversion targeted to a specific color space for each point. In this case, the color reproducibility for the target color space is improved.

Also, although the example of the color conversion by using the HSL space is described above, it is also possible to similarly perform the color conversion by using cubic 3D-LUT also in another color space of YCbCr and RGB. For example, the color is divided into two axes in a case of the YCbCr space; however, the hue is on one axis in a case of the HSL space, so that the color is easily understood and the color conversion may be easily performed.

As described above, according to the present technology, it is possible to obtain the image in which the color reproduction is optimized and the image in which the color discrimination is improved according to an environment and the subject.

As for the image in which the color reproduction is optimized, the color conversion parameter for performing optimal color reproduction each time the subject and the environment change is generated, and it is possible to maintain the output image having the optimal color reproduction.

As for the image in which the color discrimination is improved, the color conversion parameter such that the color discrimination increases depending on the light source and the color distribution of the subject is generated, so that the image with high color discrimination is output by a process of spreading minute change in color also for the image with deteriorated color discrimination generally occupied with the similar colors. Also, the process is adaptively changed according to the conversion of the input image and it is possible to perform the process always with the optimal color conversion parameter.

Meanwhile, the present technology may be applied not only to the endoscope system but also to any device for medical use and non-medical use as long as the device processes the image biased to the specific color system.

The above-described series of processes may be executed by hardware or by software. When a series of processes is performed by the software, a program which forms the software is installed on a computer. Herein, the computer includes a computer embedded in dedicated hardware and a general-purpose personal computer capable of executing various functions by various programs installed.

<Second Embodiment>

[Configuration Example of Computer]

Figure 9:
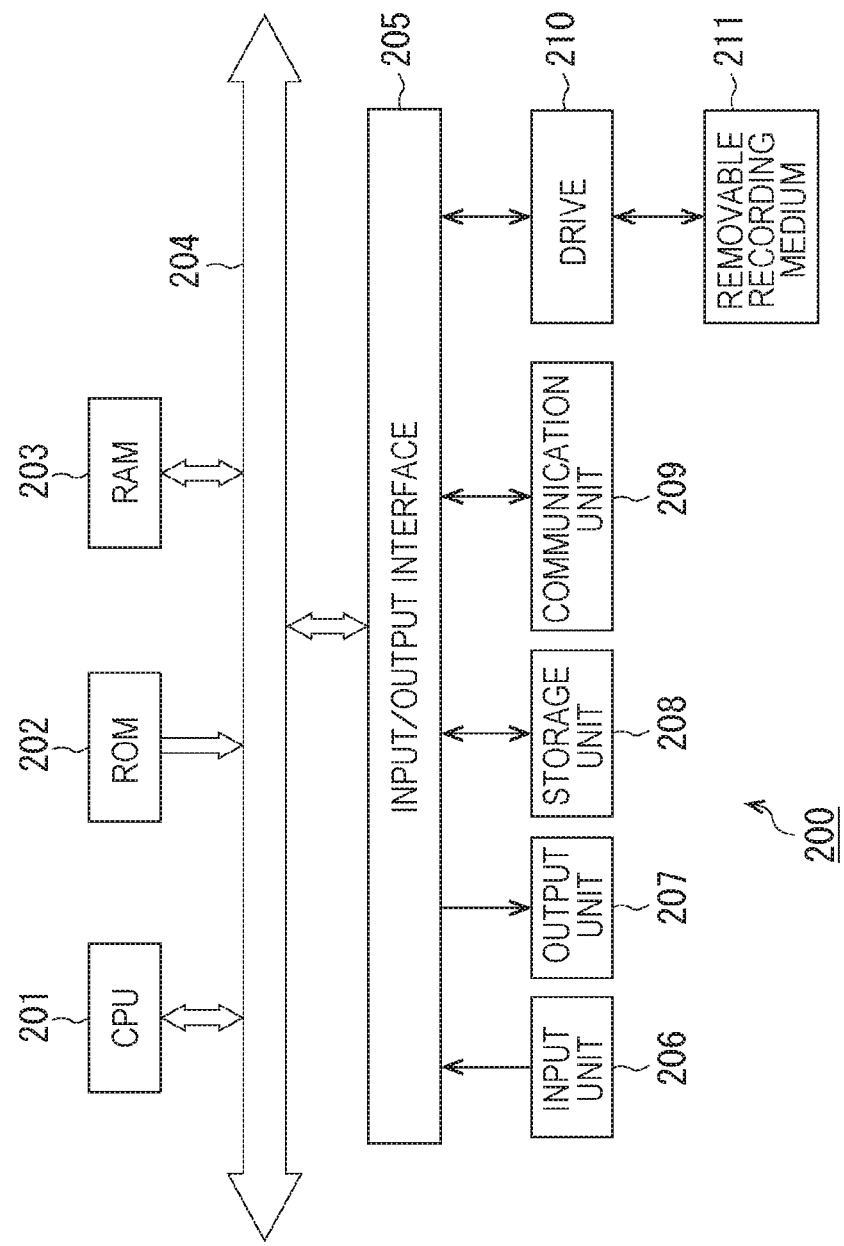
FIG. 9 is a block diagram illustrating a configuration example of a computer.

FIG. 9 is a block diagram illustrating a configuration example of hardware of a computer which executes the above-described series of processes by a program.

In a computer 200, a central processing unit (CPU) 201, a read only memory (ROM) 202, and a random access memory (RAM) 203 are connected to one another through a bus 204.

An input/output interface 205 is further connected to the bus 204. An input unit 206, an output unit 207, a storage unit 208, a communication unit 209, and a drive 210 are connected to the input/output interface 205.

The input unit 206 is formed of a keyboard, a mouse, a microphone and the like. The output unit 207 is formed of a display, a speaker and the like. The storage unit 208 is formed of a hard disk, a non-volatile memory and the like. The communication unit 209 is formed of a network interface and the like. The drive 210 drives a removable recording medium 211 such as a magnetic disc, an optical disc, a magnetooptical disc or a semiconductor memory.

In the computer configured in the above-described manner, the CPU 201 loads the program stored in the storage unit 208 on the RAM 203 through the input/output interface 205 and the bus 204 to execute, for example, and according to this, the above-described series of processes is performed.

The program executed by the computer (CPU 201) may be recorded in the removable recording medium 211 as a package medium and the like to be provided, for example. Also, the program may be provided through a wired or wireless transmission medium such as a local area network, the Internet, digital broadcasting and the like.

In the computer, the program may be installed on the storage unit 208 through the input/output interface 205 by mounting the removable recording medium 211 on the drive 210. Also, the program may be received by the communication unit 209 through the wired or wireless transmission medium to be installed on the storage unit 208. In addition, the program may be installed in advance on the ROM 202 and the storage unit 208.

Meanwhile, the program executed by the computer may be the program processes of which are performed in chronological order in the order described in this specification or may be the program the processes of which are performed in parallel or at required timing such as when a call is issued.

Also, in this specification, the term "system" is intended to mean an integral apparatus formed of a plurality of apparatuses, blocks, and means.

Meanwhile, the embodiment in the present disclosure is not limited to the above-described embodiments; various modifications may be made without departing from the scope of the present disclosure.

Although the preferred embodiments of the present disclosure are described above in detail with reference to the attached drawings, the disclosure is not limited to such examples. It is clear that one of ordinary skill in the field of the technology to which the present disclosure belongs may conceive of various modifications and corrections within the scope of the technical idea recited in claims and it is understood that they also naturally belong to the technical scope of the present disclosure.

Meanwhile, the present technology may also have the following configurations.

(1) An image processing apparatus including:

a histogram generation unit which generates a histogram of pixel values for an input image biased to a specific color system; and a parameter generation unit which generates a color conversion parameter for a color conversion process on the input image by arranging a point of a grid in a space of 3D-LUT on the basis of the histogram generated by the histogram generation unit.

(2) The image processing apparatus according to (1) described above, further including:

a histogram correction unit which corrects the histogram generated by the histogram generation unit by using a standard histogram of pixel values obtained according to statistics of an image biased to the specific color system.

(3) The image processing apparatus according to claims (1) or (2) described above, further including:

a foreign object detection unit which detects a foreign object from the image, wherein the histogram correction unit corrects the histogram generated by the histogram generation unit by eliminating the foreign object detected by the foreign object detection.

(4) The image processing apparatus according to (1) or (2) described above, further including:

a light source estimation unit which estimates a light source from the histogram generated by the histogram generation unit, wherein the histogram correction unit corrects the histogram generated by the histogram generation unit according to the light source estimated by the light source estimation unit.

(5) The image processing apparatus according to any one of (1) to (4) described above, wherein the histogram of the pixel values is the histogram regarding at least a color.

(6) The image processing apparatus according to any one of (1) to (4) described above, wherein the histogram of the pixel values is the histogram regarding hue, saturation, and luminance.

(7) The image processing apparatus according to any one of (1) to (6) described above, wherein the histogram correction unit corrects the histogram generated by the histogram generation unit by obtaining a product of the histogram generated by the histogram generation unit and the standard histogram to weight.

(8) The image processing apparatus according to any one of (1) to (7) described above, wherein the parameter generation unit densely arranges points of the grid in the space of the LUT for a portion with high frequency.

(9) The image processing apparatus according to (8) described above, wherein the input image is the image biased to reddish colors, and the parameter generation unit densely arranges the points of the grid in the space of the LUT for the reddish colors.

(10) The image processing apparatus according to (8) described above, wherein the input image is the image biased to whitish colors, and the parameter generation unit densely arranges the points of the grid in the space of the LUT for the whitish colors.

(11) The image processing apparatus according to (8) described above, wherein the input image is the image biased to yellowish colors, and the parameter generation unit densely arranges the points of the grid in the space of the LUT for the yellowish colors.

(12) The image processing apparatus according to any one of (1) to (11) described above, wherein the parameter generation unit generates the color conversion parameter by displacing distribution of the points of the grid arranged in the space of the LUT.

(13) The image processing apparatus according to any one of (3) to (11) described above, wherein the foreign object detection unit detects the foreign object from the image by using the histogram generated by the histogram generation unit and the standard histogram.

(14) The image processing apparatus according to any one of (1) to (13) described above, further including:

a standard histogram selection unit which selects the standard histogram according to the light source, wherein the histogram correction unit corrects the histogram generated by the histogram generation unit by using the standard histogram selected by the standard histogram selection unit.

(15) The image processing apparatus according to (14) described above, further including:

a light source estimation unit which estimates the light source from the histogram generated by the histogram generation unit, wherein the standard histogram selection unit selects the standard histogram according to the light source estimated by the light source estimation unit.

(16) The image processing apparatus according to any one of (1) to (15) described above, further including:

a color conversion processor which performs a color conversion process on the input image according to the parameter generated by the parameter generation unit.

(17) An image processing method, wherein an image processing apparatus generates a histogram of pixel values for an input image biased to a specific color system, and generates a color conversion parameter for a color conversion process on the input image by arranging a point of a grid in a space of 3D-LUT on the basis of the generated histogram.

(18) A program which allows a computer to serve as:

a histogram generation unit which generates a histogram of pixel values for an input image biased to a specific color system; and a parameter generation unit which generates a color conversion parameter for a color conversion process on the input image by arranging a point of a grid in a space of 3D-LUT on the basis of the histogram generated by the histogram generation unit.

(19) An endoscope system including:

a scope;

a camera head;

a histogram generation unit which generates a histogram of pixel values for an input image biased to a specific color system input from the camera head through the scope; and a parameter generation unit which generates a color conversion parameter for a color conversion process on the input image by arranging a point of a grid in a space of 3D-LUT on the basis of the histogram generated by the histogram generation unit.

REFERENCE SIGNS LIST

11 Endoscope system
21 Scope
22 Camera head
23 Light source unit
24 CCU

25 Monitor
31 Signal processor
32 Detection unit
33 Memory
51 Histogram generation unit
52 Light source estimation unit
53 Living body image standard histogram selection unit
54 Foreign object detection unit
55 Histogram generation unit
56 Conversion parameter generation unit
57 Conversion processor

The invention claimed is:

1. An image processing apparatus comprising:
a camera head;
a display; and
a camera controller including a signal processor configured to
generate one or more histograms of pixel values for an input image biased to a specific color system, the input image being received via the camera head,
detect a foreign object from the input image based upon a comparison of each of the one or more generated histograms and a corresponding standard histogram obtained according to statistics of an image biased to the specific color system,
correct each of the one or more generated histograms by obtaining a product of each of the one or more generated histograms and the corresponding standard histogram by weight, wherein pixel values corresponding to the detected foreign object are subtracted from each of the one or more generated histograms,
arrange a point of a grid in a color space of a 3D-LUT based upon the one or more corrected generated histograms, the arrangement of the point of the grid being based upon a frequency, in each of the one or more corrected generated histograms, of pixel values of one or more components of the color space of the 3D-LUT,
generate a color conversion parameter based upon the arrangement of the point of the grid in the color space of the 3D-LUT for a color conversion process on the input image, and
control display of an output image on the display based upon the color conversion process on the input image, wherein
the one or more components of the color space of the 3D-LUT include a hue component, a saturation component, and a luminance component,
the color conversion parameter defines a displacement parameter of the point of the grid in the color space of the 3D-LUT, and
a subsequent arrangement of the grid in the color space of the 3D-LUT is based upon the displacement parameter.

2. The image processing apparatus according to claim 1, wherein
the corresponding standard histogram comprises pixel values obtained according to statistics of the image biased to the specific color system.

3. The image process apparatus according to claim 2, wherein the signal processor is further configured to
estimate a light source from each of the one or more generated histograms, wherein
each of the one or more generated histograms is corrected according to the estimated light source.

4. The image processing apparatus according to claim 1, wherein
each of the one or more generated histograms of pixel values is a histogram regarding at least a color.

5. The image processing apparatus according to claim 1, wherein
each of the one or more generated histograms of pixel values is a histogram regarding the hue component, the saturation component, and the luminance component.

6. The image processing apparatus according to claim 1, wherein the signal processor is further configured to
densely arrange one or more points of the grid in the color space of the 3D-LUT for a portion with high frequency.

7. The image processing apparatus according to claim 6, wherein
the input image is an image biased to reddish colors, and
the signal processor is further configured to densely arrange the one or more points of the grid in the color space of the 3D-LUT for the reddish colors.

8. The image processing apparatus according to claim 6, wherein
the input image is an image biased to whitish colors, and
the signal processor is further configured to densely arrange the one or more points of the grid in the color space of the 3D-LUT for the whitish colors.

9. The image processing apparatus according to claim 6, wherein
the input image is an image biased to yellowish colors, and
the signal processor is further configured to densely arrange the one or more points of the grid in the color space of the 3D-LUT for the yellowish colors.

10. The image processing apparatus according to claim 2, wherein the signal processor is further configured to:
select the corresponding standard histogram according to a light source, wherein
each of the one or more generated histograms is corrected by using the selected corresponding standard histogram.

11. The image processing apparatus according to claim 10, wherein the signal processor is further configured to:
estimate the light source from each of the one or more generated histograms, wherein
the selected corresponding standard histogram being selected according to an estimated light source, the estimated light source being estimated from each of the one or more generated histograms.

12. An image processing method of an image processing apparatus, comprising:
generating, by signal processor, one or more histograms of pixel values for an input image biased to a specific color system, the input image being received via a camera head;
detecting, by the signal processing, a foreign object from the input image based upon a comparison of each of the one or more generated histograms and a corresponding standard histogram obtained according to statistics of an image biased to the specific color system;
correcting, by the signal processor, each of the one or more generated histograms by obtaining a product of each of the one or more generated histograms and the corresponding standard histogram by weight, wherein pixel values corresponding to the detected foreign object are subtracted from each of the one or more generated histograms;
arranging, by the signal processor, a point of a grid in a color space of a 3D-LUT based upon the one or more corrected generated histograms, the arranging of the point being based upon a frequency, in each of the one or more corrected generated histograms, of pixel values of one or more components of the color space of the 3D-LUT;

generating, by the signal processor, a color conversion parameter based upon the arranging of the point of the grid in the color space of the 3D-LUT for a color conversion process on the input image; and controlling, by the signal processor, display of an output image on a display based upon the color conversion process on the input image, wherein the one or more components of the color space of the 3D-LUT include a hue component, a saturation component, and a luminance component, the color conversion parameter defines a displacement parameter of the point of the grid in the color space of the 3D-LUT, and a subsequent arrangement of the grid in the color space of the 3D-LUT is based upon the displacement parameter.

13. A non-transitory computer-readable storage medium storing computer-readable instructions that, when executed by a computer, cause the computer to perform an image processing method of an image processing apparatus, comprising:

generating one or more histograms of pixel values for an input image biased to a specific color system, the input image being received via a camera head;

detecting a foreign object from the input image based upon a comparison of each of the one or more generated histograms and a corresponding standard histogram obtained according to statistics of an image biased to the specific color system;

correcting each of the one or more generated histograms by obtaining a product of each of the one or more generated histograms and the corresponding standard histogram by weight, wherein pixel values corresponding to the detected foreign object are subtracted from each of the one or more generated histograms;

arranging a point of a grid in a color space of a 3D-LUT based upon the one or more corrected generated histograms, the arranging of the point being based upon a frequency, in each of the one or more corrected generated histograms, of pixel values of one or more components of the color space of the 3D-LUT;

generating a color conversion parameter based upon the arranging of the point of the grid in the color space of the 3D-LUT for a color conversion process on the input image; and controlling display of an output image on a display based upon the color conversion process on the input image, wherein the one or more components of the color space of the 3D-LUT include a hue component, a saturation component, and a luminance component, the color conversion parameter defines a displacement parameter of the point of the grid in the color space of the 3D-LUT, and a subsequent arrangement of the grid in the color space of the 3D-LUT is based upon the displacement parameter.

14. An endoscope system, comprising:

an endoscope;

a camera head;

a display; and a camera control unit including a signal processor configured to generate one or more histograms of pixel values for an input image biased to a specific color system received from the camera head through the endoscope, detect a foreign object from the input image based upon a comparison of each of the one or more generated histograms and a corresponding standard histogram obtained according to statistics of an image biased to the specific color system, correct each of the one or more generated histograms by obtaining a product of each of the one or more generated histograms and the corresponding standard histogram by weight, wherein pixel values corresponding to the detected foreign object are subtracted from each of the one or more generated histograms, arrange a point of a grid in a color space of a 3D-LUT based upon the one or more corrected generated histograms, the arrangement of the point of the grid being based upon a frequency, in each of the one or more corrected generated histograms, of pixel values of one or more components of the color space of the 3D-LUT, generate a color conversion parameter based upon the arrangement of the point of the grid in the color space of the 3D-LUT for a color conversion process on the input image, and control display of an output image on the display based upon the color conversion process on the input image, wherein the one or more components of the color space of the 3D-LUT include a hue component, a saturation component, and a luminance component, the color conversion parameter defines a displacement parameter of the point of the grid in the color space of the 3D-LUT, and a subsequent arrangement of the grid in the color space of the 3D-LUT is based upon the displacement parameter.

* * * * *